United States Patent [19]

Pearce, Jr. et al.

[11] 4,123,131
[45] Oct. 31, 1978

[54] VENTED ELECTRICAL CONNECTOR

[75] Inventors: Warren Pearce, Jr., Warren; Andrew Russo, Jr., Fowler, both of Ohio

[73] Assignee: General Motors Corporation, Detroit, Mich.

[21] Appl. No.: 822,135

[22] Filed: Aug. 5, 1977

[51] Int. Cl.² ............................................. H01R 3/04
[52] U.S. Cl. .............................. 339/117 R; 204/195 S; 339/213 R; 339/217 R
[58] Field of Search ........... 339/117 R, 117 P, 118 R, 339/213 R, 217 R; 204/195 S

[56] References Cited
U.S. PATENT DOCUMENTS

| | | | |
|---|---|---|---|
| 3,037,183 | 5/1962 | Hopkins | 339/213 R |
| 3,844,920 | 10/1974 | Burgett et al. | 204/195 S |
| 3,960,693 | 6/1976 | Weyl et al. | 204/195 S |

*Primary Examiner*—Roy Lake
*Assistant Examiner*—DeWalden W. Jones
*Attorney, Agent, or Firm*—F. J. Fodale

[57] ABSTRACT

An electrical connector is matably attached to an oxygen sensor having a hollow center terminal for exposing the inner electrode of the oxygen sensor to ambient air. The electrical connector comprises a nylon connector body having radially spaced shrouds at a plug-in opening which receives the oxygen sensor terminal. A silicone rubber seal sleeve disposed in the outer shroud sealingly engages the inner shroud and the insulator sleeve of the oxygen sensor to environmentally protect the interface between the oxygen sensor terminal and the mating terminal carried by the connector body. The plug-in opening is vented via grooves in the shrouds. A retaining clip carried by the outer shroud forms a splash shield for the vent inlet. The connector body has an enlarged lead receiving opening which is sealed by a seal sleeve molded on the lead.

4 Claims, 5 Drawing Figures

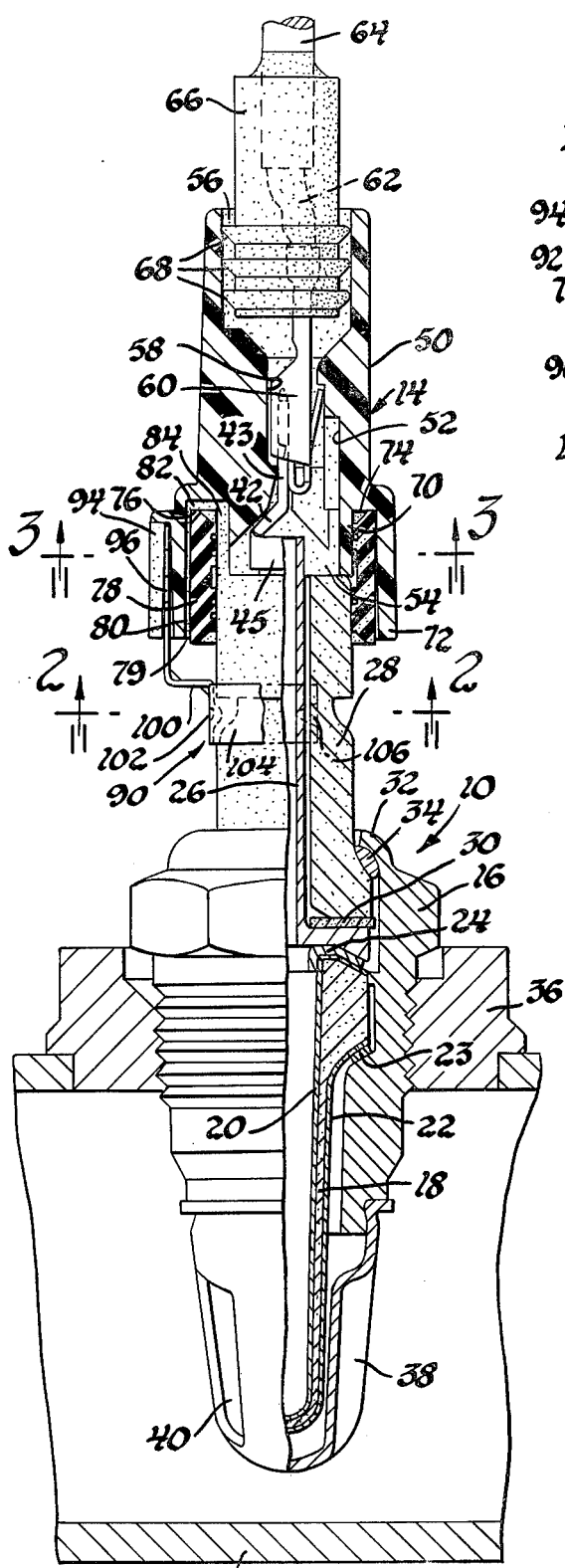
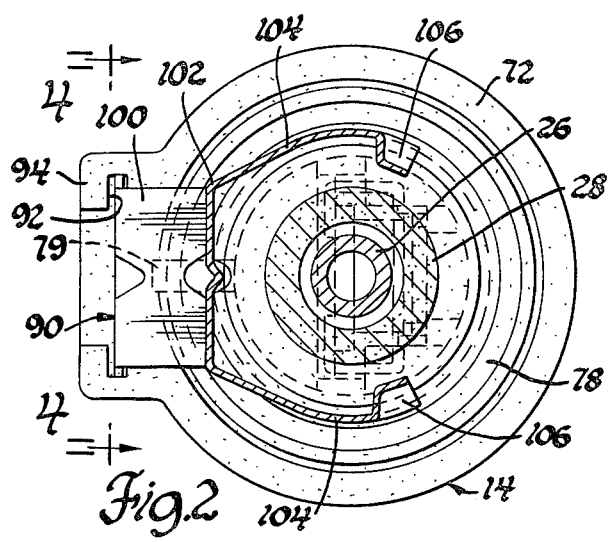
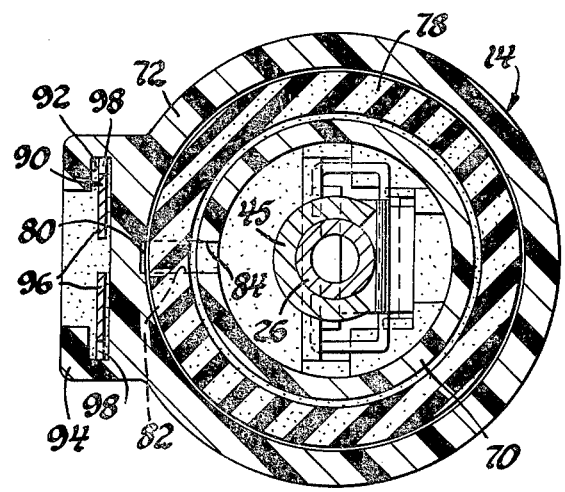
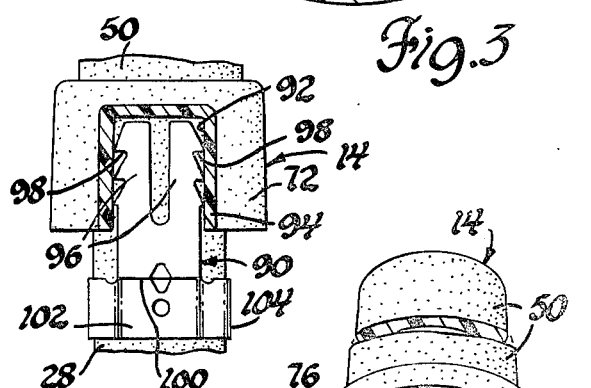
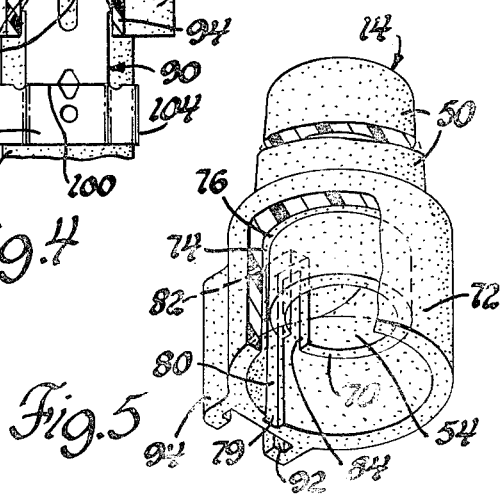

VENTED ELECTRICAL CONNECTOR

This invention relates to vented electrical connectors and more particularly to a vented electrical connector for an oxygen sensor or the like.

An oxygen sensor is a known device for monitoring or controlling the air to fuel ratio of the combustible mixture delivered to the intake of an internal combustion engine. This ratio effects the amount of emissions in the exhaust gases, some of which in the case of automotive vehicles must be maintained at or below certain levels prescribed by the United States government.

One known type of oxygen sensor utilizes an inner electrode which is exposed to ambient air via a hollow center terminal and an outer electrode which is exposed to the exhaust gases of an internal combustion engine. This device produces a low level electrical signal responsive to the relative concentrations of oxygen at the inner and outer electrodes.

The object of this invention is to provide a vented electrical connector suitable for use with such an oxygen sensor or a like electrical device when it is located in a harsh environment such as is found in the vicinity of the engine of an automotive vehicle.

Another object of this invention is to provide a vented electrical connector which can operate in the vicinity of an internal combustion engine where temperatures reach as high as 300° F. or more.

Yet another object of this invention is to provide a vented electrical connector for an electrical device which generates low level electrical signals and has a hollow center terminal for exposing an internal component to ambient air.

Other objects and features of the invention will become apparent to those skilled in the art as the disclosure is made in the following detailed description of a preferred embodiment of the invention as illustrated in the accompanying sheet of drawings in which:

FIG. 1 is a partially sectioned elevation view of an oxygen sensor having an attached electrical connector in accordance with this invention.

FIG. 2 is a section taken substantially along the line 2—2 of FIG. 1 and looking in the direction of the arrows.

FIG. 3 is a section taken substantially along the line 3—3 of FIG. 1 and looking in the direction of the arrows.

FIG. 4 is a view taken substantially along the line 4—4 of FIG. 2 and looking in the direction of the arrows.

FIG. 5 is a partially sectioned perspective view of a component of the electrical connector shown in FIG. 1.

Referring now to the drawing and more particularly to FIG. 1 there is shown an oxygen sensor 10 mounted to an exhaust conduit 12. The lower end of the oxygen sensor 10 is disposed in the exhaust conduit and produces an electrical signal responsive to the presence of certain constituents in the exhaust gases passing through the conduit. The electrical signal is transmitted to suitable control or monitoring equipment (not shown) via the electrical connector 14 which is the subject of this invention.

By way of background present government policy dictates maintaining low levels of various automotive exhaust gas emissions such as unburned hydrocarbons, oxides of nitrogen and carbon monoxide. These emissions are a function of the air to fuel ratio of the combustible mixture taken in by a particular internal combustion engine. One approach to meeting government standards then is the maintenance of desired air to fuel ratios during the operation of the engine so that predictable amounts of emissions are produced which are either within the prescribed levels or capable of being further reduced to prescribed levels by other devices such as a catalytic converter.

A well known device for generating an appropriate signal to control the air to fuel ratio of the combustible mixture taken in by the engine is an oxygen sensor which is in part exposed to the engine exhaust gases such as the oxygen sensor shown in FIG. 1 or the oxygen sensor disclosed in U.S. Pat. No. 3,844,920 granted to Richard R. Burgett and Bruce W. Holleboom on Oct. 29, 1974 for an "Air Fuel Ratio Sensor".

Returning to the drawing, particularly FIG. 1, the oxygen sensor 10 comprises an outer metal shell 16 and a hollow zirconia element 18. The zirconia element 18 has an inner electrode 20 formed by a platinum coating on its inner and top surfaces. A discrete platinum coating on the outer surface forms an outer electrode 22. The use of catalytic materials such as platinum for the electrodes in oxygen sensors is well known.

The hollow zirconia element 18 with its coated electrodes is supported by an internal shoulder of the outer metal shell 16. An interposed copper sealing ring 23 establishes an electrically conductive path from the outer electrode 22 and to the outer metal shell 16. Another copper sealing ring 24 sits atop the element 18 in electrical contact with the inner electrode 20. The base of a hollow center terminal 26 rests on the copper sealing ring 24 and in turn supports an alumina insulator sleeve 28. An interposed mica seal washer 30 accommodates differential thermal expansion of the internal components which are firmly seated in the outer metal shell 16 by an inturned lip 32 deformed against a steel ring 34 surrounding the enlarged lower end of the insulator sleeve 28. When the oxygen sensor 10 is threadably secured to an appropriate mounting boss 36 the electrode 22 is exposed to the exhaust gases in the conduit 12 and the inner electrode 20 is exposed to ambient air via the hollow center terminal 26.

The oxygen sensor 10 may also include a shield 38 having inlets 40 to protect the protruding lower portion of the zirconia element 18 while providing exposure of the outer electrode 22 to the exhaust gases. The oxygen sensor 10 may also include a more conventional interface terminal 42 comprising a standardly configured male blade 43 and a part circular base 45 welded to the outer surface of the exposed tip of the hollow center terminal 26.

Briefly the oxygen sensor operates as a miniature electrochemical voltaic cell. The zirconia element is an ion conducting solid electrolyte which when activated by the heat of the exhaust gases or otherwise conducts oxygen ions collected from the ambient air in the hollow zirconia element 18 by the inner electrode 20 to the outer electrode 22 developing a potential difference or voltage between the two electrodes. The amount of voltage which is generated is related to and thus indicative of the concentration of oxygen in the exhaust gases at the outer electrode 22 compared to the concentration of oxygen in the ambient air at the inner electrode 20. When the air to fuel ratio of the combustible mixture is very lean, the amount of oxygen in the mixture which is consumed is low and thus the oxygen concentration in the exhaust gases is nearly that of the ambient air and the generated voltage is near zero. For very rich air to fuel ratios, the amount of oxygen in the mixture which is consumed is high and the exhaust gases contain considerable oxidizable gases such as unburned hydrocarbons and carbon monoxide. This results in a very low oxygen concentration at the surface of the outer electrode 22 and the generated voltage is high relatively speaking. Thus the oxygen sensor generates a voltage signal which is indicative of the relative concentrations of oxygen at the respective electrodes which in turn is indicative of amounts of undesirable emissions in the exhaust gases. This voltage signal can then be used to monitor the air to fuel ratio of the mixture at the engine intake and to make necessary adjustments to maintain the desired emission levels.

The signal voltages generated by the oxygen sensor are a few hundred millivolts and it is generally desirable to locate the oxygen sensor as far upstream in the exhaust gases as possible, that is in the engine exhaust manifold in close proximity to the engine.

Thus the electrical connector for the oxygen sensor has stringent, somewhat diverse requirements. Due to the low level electrical signal generated by the oxygen sensor, the electrical interface between the sensor and connector terminals must be maintained extremely clean in the particularly harsh environment of an engine compartment where temperatures reach 300° F. or more, where dirt and grime accumulate, and where the effects of road splash are experienced. Not only must the electrical connector environmentally protect the electrical interface in a harsh environment, it must also provide a vent for ambient air to reach the inner electrode for proper operation of the oxygen sensor.

The electrical connector 14 in accordance with this invention meets these requirements as will hereinafter more fully appear in the following detailed description.

The electrical connector 14 comprises a connector body 50 of a temperature resistant, electrically insulative, moldable thermosetting material such as a high temperature nylon which is characteristically relatively rigid and difficult to mold in situ. High temperature nylons capable of operation in temperatures of 300° F. or more are known.

The connector body 50 has a terminal receiving cavity 52 extending therethrough from a plug-in opening 54 adapted to receive the oxygen sensor terminal 42 to an enlarged lead receiving opening 56. The mid portion 58 of the cavity 52 is suitably configured to receive and retain a mating terminal 60 inserted through the enlarged lead receiving opening 56. The mating terminal 60 is a conventional female terminal of the type disclosed in the U.S. Pat. No. 3,037,183 granted to Joseph H. Hopkins on May 29, 1962 for an "Electric Terminal Means". The female terminal 60 includes a conventional attachment portion comprising core and insulator crimp wings which are crimped about the core (not shown) and inner insulation layer 62 of a jacketed high temperature cable or electrical lead 64. The attachment portion of the terminal 60 and the adjacent end portion of the cable 64 have a molded on seal sleeve 66 of a temperature resistant elastomeric material which matches or is compatible with the outer jacket of the high temperature cable 64 so that a bond and hermetic seal is formed therebetween. It is believed that thermoplastic synthetic rubber materials such as neoprene capable of operation up to about 250° F. are suitable since the seal sleeve 66 and cable 64 are spaced from the engine and exhaust conduit 12. The seal sleeve 66 has three annular lips 68 which sealingly engage the enlarged lead receiving opening 56.

The connector body 50 has an inner shroud 70 at the plug-in opening 54 and an outer shroud 72 radially spaced therefrom to form an annular chamber 74 having an end wall 76. The outer shroud 72 projects beyond the inner shroud 70 to protect a seal sleeve 78 of temperature resistant elastomeric thermosetting material, such as silicone rubber which is capable of operation in temperatures in excess of 300° F. The seal sleeve 78 has three internal ribs at one end portion which sealingly engage the outer surface of the inner shroud 70 and preferably the sleeve end portion is slightly stretched circumferentially. The end face of the sleeve 78 preferably sealingly engages the end wall 76 of the chamber 74.

The opposite end portion of the sleeve 78 projecting beyond the inner shroud 70 also has three internal ribs which sealingly engage the insulator sleeve 28 of the oxygen sensor 10 when the electrical connector 14 is attached to it. This end portion is also preferably slightly stretched circumferentially.

The electrical connector 14 has a vent means whereby ambient air is admitted through the hollow center terminal 26 to the hollow zirconia element 18 for reaction with the inner electrode 20 and proper functioning of the oxygen sensor.

The vent means comprises a longitudinal groove 80 in the inner surface of the outer shroud 72 leading from an inlet 79 to a communicating radial groove 82 in the end wall 76. The radial groove 82 in turn communicates with a longitudinal groove 84 in the outer surface of the inner shroud 70. The portion of the groove 84 remote from the radial groove 82 extends radially through the inner shroud 70 to communicate with the plug-in opening 54 receiving the hollow center terminal 26 of the oxygen sensor 10. Thus the vent means while being a rather circuitous path from the ambient air to minimize contamination of the electrical interfaces between the terminals 42 and 60 is rather easy to mold because the grooves are shaped to be formed by a longitudinally withdrawable mold part. The electrical connector 14 is normally vertically disposed as shown in FIG. 1 so that the initial portion of the vent means (groove 80) extends vertically upward as a further safeguard.

The electrical connector 14 is latched to the oxygen sensor by a sheet metal locking clip 90 mounted in a transverse slot 92 in a boss 94 on the outer shroud 72. The base 96 of the clip 90 is flat and has a bifurcated end having saw tooth edges 98 which bite into the edges defining the slot 92 to fasten the locking clip to the connector body. A transverse or radial portion 100 at the opposite end of the base 96 carries a latch portion 102 having a pair of resilient arms 104 each having a detent 106 at its free end. The detents 106 snap into a cooperating groove in the insulator sleeve 28 under the action of the resilient arms 104 when the electrical connector 14 is attached to the oxygen sensor 10. The protruding portion of the base 96 and the transverse portion 100 are wide and thus form a splash shield for the vent inlet 79 providing still further protection. The boss 94 also serves as an index means to align the terminals 42 and 60 for attachment.

We wish it to be understood that we do not desire to be limited to the exact details of construction shown and described, for obvious modifications will occur to a person skilled in the art.

What is claimed is:

1. An electrical connector for providing an environmentally protected, vented, temperature resistant electrical connection to an oxygen sensor or a like electrical device generating a low level electrical signal produced at least in part by means exposed to ambient air comprising:

a connector body of a relatively rigid, temperature resistant synthetic material, said connector body having a terminal receiving cavity extending therethrough from a plug-in opening to a lead receiving opening, said connector body having an inner shroud at the plug-in opening of the terminal receiving cavity and an outer shroud radially spaced therefrom to form an annular chamber having an end wall, said outer shroud projecting beyond the inner shroud, a seal sleeve of temperature resistant elastomeric material disposed in said chamber in sealing engagement with an outer surface of the inner shroud, said seal sleeve having a portion projecting beyond the inner shroud which portion has an inner surface adapted to receive and sealingly engage an insulator sleeve surrounding a hollow protruding center terminal of an oxygen sensor or like electrical device, and vent means leading from an inlet at an exposed surface of the connector body to the terminal receiving cavity, said vent means including a radial passage through the inner shroud.

2. An electrical connector for providing an environmentally protected, vented, temperature resistant electrical connection to an oxygen sensor or a like electrical device generating a low level electrical signal produced at least in part by means exposed to ambient air comprising:

a connector body of a relatively rigid, temperature resistant synthetic material, said connector body having a terminal receiving cavity extending therethrough from a plug-in opening adapted to receive a protruding hollow center terminal of an oxygen sensor or the like to a lead receiving opening, said connector body having an inner shroud at the plug-in opening of the terminal receiving cavity and an outer shroud radially spaced therefrom to form an annular chamber having an end wall, said outer shroud projecting beyond the inner shroud, a seal sleeve of temperature resistant elastomeric material disposed in said chamber in sealing engagement with an outer surface of the inner shroud, said seal sleeve having a portion projecting beyond the inner shroud which portion has an inner surface adapted to receive and sealingly engage an insulator sleeve adjacent the protruding hollow center terminal of the oxygen sensor or like electrical device, and vent means leading from an inlet at an exposed surface of the outer shroud to the terminal receiving cavity, said vent means including a passage between an end face of the seal sleeve and the end wall of the chamber and a longitudinal groove in the outer surface of the inner shroud having a portion which extends radially through the inner shroud to the plug-in opening of the terminal receiving cavity.

3. An electrical connector for providing an environmentally protected, vented, temperature resistant electrical connection to an oxygen sensor or a like electrical device generating a low level electrical signal produced at least in part by means exposed to ambient air comprising:

a connector body of a relatively rigid, temperature resistant synthetic material, said connector body having a terminal receiving cavity extending therethrough from a plug-in opening adapted to receive a protruding hollow center terminal of an oxygen sensor or the like, to a lead receiving opening, said connector body having an inner shroud at the plug-in opening of the terminal receiving cavity and an outer shroud radially spaced therefrom to form an annular chamber having an end wall, said outer shroud projecting beyond the inner shroud to substantially protect a seal sleeve of temperature resistant elastomeric material disposed in said chamber in sealing engagement with an outer surface of the inner shroud, said seal sleeve being adapted to seal against the end wall of the chamber and having a portion projecting beyond the inner shroud which portion has an inner surface adapted to receive and sealingly engage an insulated portion adjacent the protruding hollow center terminal of the oxygen sensor or like electrical device, and vent means leading from an inlet at an exposed end surface of the outer shroud to the plug-in opening of the terminal receiving cavity, said vent means including a longitudinal groove in the bore of the outer shroud, a longitudinal groove in the outer surface of the inner shroud, and an interconnecting passage between an end face of the seal sleeve and the end wall of the chamber.

4. An electrical connector for providing an environmentally protected, vented, temperature resistant electrical connection to an oxygen sensor or a like electrical device generating a low level electrical signal produced at least in part by means exposed to ambient air comprising:

a connector body of a relatively rigid, temperature resistant synthetic material, said connector body having a terminal receiving cavity extending therethrough from a plug-in opening adapted to receive a protruding hollow center terminal of an oxygen sensor or the like, to a lead receiving opening, said connector body having an inner shroud at the plug-in opening of the terminal receiving cavity and an outer shroud radially spaced therefrom to form an annular chamber having an end wall, said outer shroud projecting beyond the inner shroud to substantially protect a seal sleeve of temperature resistant elastomeric material disposed in said chamber in sealing engagement with an outer surface of the inner shroud, said seal sleeve being adapted to seal against the end wall of the chamber and having a portion projecting beyond the inner shroud which portion has an inner surface adapted to receive and sealingly engage an insulated portion adjacent the protruding hollow center terminal of the oxygen sensor or like electrical device, vent means leading from an inlet at an exposed end surface of the outer shroud to the plug-in opening of the terminal receiving cavity, said vent means comprising a longitudinal groove in the bore of the outer shroud, a radial groove in the end wall of the chamber and a longitudinal groove in the outer surface of the inner shroud in radial alignment, said last mentioned longitudinal groove having an end portion remote from said end wall which extends radially through said inner shroud, and a locking clip mounted on the outer shroud having longitudinal and transverse portions spaced from said inlet forming a splash shield for the inlet.

* * * * *